United States Patent [19]

Fikentscher et al.

[11] Patent Number: 4,978,780
[45] Date of Patent: Dec. 18, 1990

[54] PREPARATION OF ETHER SULFONATES AND POLYGLYCOL ETHER SULFONATES, AND PRODUCTS PREPARED BY THIS METHOD

[75] Inventors: Rolf Fikentscher, Ludwigshafen; Norbert Greif, Bobenheim; Knut Oppenlaender, Ludwigshafen; Karl Stork, Lampertheim, all of Fed. Rep. of Germany

[73] Assignee: BASF Aktiengesellschaft, Ludwigshafen, Fed. Rep. of Germany

[21] Appl. No.: 405,582

[22] Filed: Sep. 11, 1989

Related U.S. Application Data

[63] Continuation of Ser. No. 257,722, Oct. 14, 1988, abandoned.

[30] Foreign Application Priority Data

Oct. 16, 1987 [DE] Fed. Rep. of Germany ....... 3735056

[51] Int. Cl.$^5$ ............................................. C07C 303/02
[52] U.S. Cl. ...................................... 562/42; 562/100; 562/110
[58] Field of Search ........................... 562/110, 42, 100

[56] References Cited

U.S. PATENT DOCUMENTS

| | | | |
|---|---|---|---|
| 2,062,958 | 5/1931 | Baldwin et al. | 260/513 R |
| 2,886,585 | 5/1959 | Barsky | 260/513 R |
| 3,190,906 | 6/1965 | Mueller et al. | 558/48 |
| 3,856,738 | 12/1974 | Bodesheim et al. | 260/513 R |
| 4,091,014 | 5/1978 | Johnson, Jr. et al. | 562/42 |
| 4,466,891 | 8/1984 | McCoy | 562/42 |

FOREIGN PATENT DOCUMENTS

| | | | |
|---|---|---|---|
| 260110 | 6/1965 | Australia | 562/110 |
| 64384 | 11/1982 | European Pat. Off. | 562/110 |

*Primary Examiner*—Gary P. Straub
*Assistant Examiner*—Stuart L. Hendrickson
*Attorney, Agent, or Firm*—Oblon, Spivak, McClelland, Maier & Neustadt

[57] ABSTRACT

A process for the preparation of ether sulfonates or polyglycol ether sulfonates by reacting an organic alcoholic or phenolic compound or the corresponding alkoxylate in aqueous solution with vinyl sulfonate in the presence of from 0.1 to 3.0% by weight of an alkaline catalyst and, if required, additionally in the presence of a phase-transfer catalyst, and ether sulfonates or polyglycol ether sulfonates prepared by this process and of the general formula

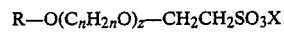

where R is H or an aliphatic or aromatic hydrocarbon radical (which may contain nitrogen as a heteroatom) of 1 to 30 carbon atoms, n is from 2 to 30, z is from 0 to 300 and X is an alkali metal.

3 Claims, No Drawings

PREPARATION OF ETHER SULFONATES AND POLYGLYCOL ETHER SULFONATES, AND PRODUCTS PREPARED BY THIS METHOD

This application is a continuation of application Ser. No. 07/257,722, filed on Oct. 14, 1988, now abandoned.

The present invention relates to a process for the preparation of ether sulfonates and polyglycol ether sulfonates by reacting an organic alcoholic or phenolic compound or the corresponding alkoxylate with an organic sulfonate component, and to ether sulfonates and polyglycol ether sulfonates prepared by this process.

Products of this type are anionic surfactants, i.e. surfactant wetting agents which are required for many purposes in technical fields and industry.

Frequently, however, the conventional anionic surfactants, such as alkylbenzenesulfonates, olefinsulfonates and paraffinsulfonates, have inadequate surfactant properties, in particular poor stability in hard water.

Anionic surfactants having a polyglycol ether chain, on the other hand, have greatly improved properties with respect to electrolyte-containing aqueous media, for example alkylpolyglycol ether sulfates and sodium salts of sulfuric half-esters of polyglycol ethers. Being esters with S—O bonds, these products are, however, unstable to hydrolysis even in weakly acidic media. However, polyglycol ether sulfonates, i.e. products having C—S bonds, should have good stability to hard water and stability to hydrolysis.

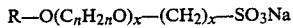

Such products are known, but the methods for their preparation are unsatisfactory.

For example, polyglycol ethers (alkoxylates) can be converted with $SOCl_2$, $PCl_3$ or $COCl_2$, via the corresponding intermediates, into the chlorides of the polyglycol ethers, which are then reacted with $Na_2SO_3$ to give the corresponding sulfonates. However, this is a very expensive method of preparation and, furthermore, corrosive products ($SO_2$, HCl) or fairly large amounts of NaCl are formed and have to be removed from the reaction mixtures; moreover, particular care is necessary when working with phosgene.

Other synthesis routes also have disadvantages. Thus, in the allyl ether route, the corresponding allyl ether must be prepared by first reacting an alkoxylate with allyl chloride (production of HCl or NaCl), the allyl ether being subjected to an addition reaction with $NaHSO_3$ in a subsequent reaction. For toxicological and economic reasons, the reaction of polyglycol ethers with propane sulfone to give the corresponding propylsulfonates is not very attractive.

A better method is the reaction of alkoxylates with hydroxyethyl sulfonate in an alkaline medium, this reaction being disclosed in DE-A-27 48 721. Here, however, the hydroxyethyl sulfonate must first be prepared from ethylene oxide and $NaHSO_3$. However, the subsequent reaction with OH-containing products does not always give good yields. Under these conditions, alkylpolyglycol ethers, alkylphenols or alkanols, for example, do not react or react giving low yields.

It is an object of the present invention to provide an improved synthesis route for obtaining ether sulfonates and polyglycol ether sulfonates, which does not have the abovementioned disadvantages and starts from products which are readily available industrially.

Ether sulfonates or polyglycol ether sulfonates as such are sufficiently well known that no further description is required. The starting compounds which are reacted, the organic alcoholic or phenolic compounds, are likewise sufficiently well known that they need not be discussed in particular. The same applies to the alkoxylates which are obtained by reacting the alcohols or phenols with epoxides, such as ethylene oxide or propylene oxide.

Suitable starting compounds are: $C_1$-$C_{30}$-alkanols, preferably $C_4$-$C_{22}$-alkanols (straight-chain or branched), phenol, cresols, mono-, di- or tri-n- or isoalkylphenols, e.g. mono-, di- or tri-tert-butylphenol, isooctyl- or nonylphenol, diisononylphenol or n- or isododecylphenol, having alkyl radicals which together may contain 1 to 100, in particular 4 to 30, carbon atoms, and the corresponding alkoxylates, diols, such as ethylene glycol, propylene glycol or bisphenol A, and etherdiols or polyetherdiols, such as di-, tri- or polyalkylene glycols, for example products of the Pluronic type, and corresponding triols (glycerol, trimethylolpropane) and other polyols (pentaerythritol or sorbitol) and their polyalkoxylates (polyetherpolyols).

1,2-epoxides, such as ethylene oxide, propylene oxide or butylene oxides (1,2-, iso- and 2,3-butylene oxide) and fairly long-chain 1,2-epoxides having alkyl radicals of up to 30 carbon atoms, such as styrene oxide, cyclohexene oxide, etc., are suitable for the alkaline or acid-catalyzed alkoxylation reaction.

The polyglycol ether chains can be in block form

...ABABABAB...

or randomly distributed (gassing with epoxide mixtures), e.g. AABABABABBAAB, etc.

The process is applicable to (alkyl)phenols and alkanols as well as their polyglycol ether derivatives. The same applies to the alkoxylation products of other classes, such as amine alkoxylates and amide alkoxylates, and all classes of substances which have a functional group with active H atoms which permit reaction with epoxides to give the corresponding OH-alkyl derivatives.

Particularly preferred, however, are polyglycol ether sulfonates of alcohols, phenols, alkylphenols and their alkoxylates.

According to the invention, the reaction to give the corresponding sulfonates is carried out using vinyl sulfonate (ether sulfonate), which is readily available industrially and is obtainable as an aqueous solution in the concentration range from 30 to 60% by weight. The reaction is carried out in aqueous solution, the alcoholic component being used in concentrated form (100%). In many cases, the temperature may be lower than the temperature of about 180° C. described in DE-A- No. 27 48 721. However, the reaction is preferably carried out at from 160° to 180° C.

In the reaction with vinyl sulfonate, the starting materials are present in a molar ratio of from 1:1 to 1:1.3 (based on reactive alcoholic OH groups), preferably in equimolar amounts. To increase the yields or the anionic or nonionic fraction in the reaction product, the vinyl sulfonate or the alcoholic component can be used in an excess of up to 50 mol %.

The reaction is always carried out in the presence of from 0.1 to 3, preferably from 0.5 to 2.0, % by weight of an alkaline catalyst, the percentages by weight being based on the alcohol component. The reaction may be carried out in the presence of a phase-transfer catalyst, preferably in amounts of from 0.2 to 2.0% by weight, based on the alcohol component. Preferred phase-transfer catalysts are quaternary ammonium salts, in particular methyltrioctylammonium chloride.

The additional use of a phase-transfer catalyst is particularly beneficial or essential when branched alkanols are used. The alkaline catalyst is preferably NaOH or KOH.

The products obtained according to the invention are of the general formula $$R\text{-}O(C_nH_{2n}O)_z\text{-}CH_2CH_2SO_3X$$

where R is H or an aliphatic or aromatic hydrocarbon radical (which may contain N as heteroatoms) of 1 to 30, preferably 1 to 22, carbon atoms, n is from 2 to 30, preferably from 2 to 4, z is from 0 to 300, preferably from 0 to 100, and X is an alkali metal, preferably Na or K.

The products can be used, inter alia, as surfactants and assistants for the detergent and cleaning agent sector, the dyeing industry, oil production, the crop protection sector, etc. General preparation:

The particular alcoholic component is reacted with an equimolar amount of vinyl sulfonate in the presence of from 0.1 to 3% by weight of an alkali metal hydroxide at 180° C. in the course of from 3 to 5 hours.

Before the addition of the vinyl sulfonate, the corresponding alkali metal alcoholate of the alcoholic component is prepared by heating for from 1 to 2 hours under reduced pressure (20 mmHg) at 180° C. Examples: cf. Table

TABLE

| Alcohol component | OHN | Vinyl sulfonate | Molar ratio | Reaction temperature °C. | Reaction time h | Alkali catalyst (% by weight, based on alcohol component) | OHN of the end product |
|---|---|---|---|---|---|---|---|
| Glycerol | 1830 | VS | 1:1 | 140 | 2.5 | 1.0 (KOH) | 435 (505 Th.) |
| Glycerol | 1830 | VS | 1:2 | 140 | 2.5 | 1.1 (KOH) | 135 (159 Th.) |
| Glycerol | 1830 | VS | 1:3 | 140 | 2.5 | 1.3 (KOH) | 43 |
| Isononylphenol × 4.6 EO | 138 | VS | 1:1 | 180 | 6.0 | 1.2 (KOH) | 18 |
| Isononylphenol | 258 | VS | 1.1:1 | 180 | 3.0 | 0.8 (KOH) | 36 |
| Isononylphenol | 258 | VS | 1.5:1 | 180 | 5.5 | 1.7 (KOH) | 32 |
| Dodecylphenol | 220 | VS | 1.2:1 | 180 | 6.0 | 1.2 (KOH) | 30 |
| Isodecanol × 7 EO | 125 | VS | 1:1 | 180 | 8.5 | 1.7 (KOH) | 16 |
| Isotridecanol | 276 | VS | 1.17:1 | 180 | 8.0 | 1.5 (KOH[1]) | 40 |
| Isotridecanol × 4.1 EO | 150 | VS | 1:1.3 | 180 | 6.5 | 1.7 (KOH) | 12 |
| Bisphenol A | 492 | VS | 1:2 | 150 | 10.0 | 1.8 (KOH) | 15 |
| Pluronic P 85 | 25 | VS | 1:2 | 180 | 4.5 | 1.6 (KOH) | 6 |

Note:
In the case of alcohols without an ether group, the progress of the reaction can be monitored via the OH number and IR spectrum (band intensity of C = C and —OH lower after the reaction, intensity of the ether band at about 1150 cm$^{-1}$ higher).
[1]0.75% of KOH
0.75% of phase-transfer catalyst (methyltrioctylammonium chloride)
OHN: OH number, determined according to DIN 53,240 and 53,783 (acetylation and hydrolysis)

We claim:

1. A process for the preparation of ether sulfonates having the formula $$R\text{-}O(C_nH_{2n}O)_z\text{-}CH_2CH_2\text{-}SO_3X$$

wherein R is H or an aliphatic or aromatic hydrocarbon group having 1 to 30 carbon atoms, n is from 2 to 30, z is from 0 to 300, and X is an alkali metal; comprising the steps:
    (a) mixing one or more compounds selected from the group consisting of $$R\text{-}O(C_nH_{2n}O)_z\text{-}H \text{ and } R\text{-}O(C_nH_{2n}O)_z\text{-}X$$

with a vinyl sulfonate salt in aqueous solution, wherein R, n, z and X are defined as given above;
    (b) adding 0.2–2.0% by weight, based on the selected polyether, of a quaternary ammonium halide phase transfer catalyst;
    (c) adding 0.1 to 3.0 by weight, based on the selected polyether, of an alkaline catalyst.

2. The process of claim 1 wherein R is H or an aliphatic or aromatic hydrocarbon radical of 1 to 22 carbon atoms, n is from 2 to 4, z is from 0 to 100 and X is Na$^+$ or K$^+$.

3. The process of claim 1 in which the reaction is carried out at a temperature from about 140°–180° C.

* * * * *

UNITED STATES PATENT AND TRADEMARK OFFICE
CERTIFICATE OF CORRECTION

PATENT NO. : 4,978,780
DATED : December 18, 1990
INVENTOR(S) : Rolf Fikentscher et al It is certified that error appears in the above-indentified patent and that said Letters Patent is hereby corrected as shown below:

On the title page, item [54], and in column 1, lines 3-4; delete,

", AND PRODUCTS PREPARED BY THIS METHOD"

Signed and Sealed this

Third Day of August, 1993

Attest:

MICHAEL K. KIRK

Attesting Officer

Acting Commissioner of Patents and Trademarks